(12) United States Patent
Zhu et al.

(10) Patent No.: US 10,294,335 B2
(45) Date of Patent: May 21, 2019

(54) PREPARATION METHOD, PRODUCT AND APPLICATION OF NON-FREE RADICAL PHOTO-CROSSLINKED HYDROGEL MATERIAL

(71) Applicant: Zhongshan Guanghe Medical Technology Co., Ltd, Zhongshan, Guangdong (CN)

(72) Inventors: Linyong Zhu, Shanghai (CN); Zhenzhen Liu, Shanghai (CN); Yang Wang, Shanghai (CN); Chunyan Bao, Shanghai (CN); Qiuning Lin, Shanghai (CN); Wei Fang, Shanghai (CN)

(73) Assignee: ZHONGSHAN GUANGHE MEDICAL TECHNOLOGY CO., LTD, Zhongshan, Guangdong (CN)

( * ) Notice: Subject to any disclaimer, the term of this patent is extended or adjusted under 35 U.S.C. 154(b) by 62 days.

(21) Appl. No.: 15/522,855

(22) PCT Filed: Nov. 23, 2015

(86) PCT No.: PCT/CN2015/095260
§ 371 (c)(1),
(2) Date: Apr. 28, 2017

(87) PCT Pub. No.: WO2016/082725
PCT Pub. Date: Jun. 2, 2016

(65) Prior Publication Data
US 2017/0313827 A1 Nov. 2, 2017

(30) Foreign Application Priority Data
Nov. 27, 2014 (CN) .......................... 2014 1 0698239

(51) Int. Cl.
| | | |
|---|---|---|
| A61L 27/52 | (2006.01) | |
| A61L 31/14 | (2006.01) | |
| A61K 8/73 | (2006.01) | |
| A61K 8/04 | (2006.01) | |
| A61K 8/45 | (2006.01) | |
| C08J 3/075 | (2006.01) | |
| A61K 47/34 | (2017.01) | |
| C08J 3/28 | (2006.01) | |
| A61K 8/02 | (2006.01) | |
| A61K 8/65 | (2006.01) | |
| A61K 9/06 | (2006.01) | |
| A61K 31/728 | (2006.01) | |
| A61K 47/36 | (2006.01) | |
| A61L 31/04 | (2006.01) | |
| A61Q 19/00 | (2006.01) | |
| A61Q 19/02 | (2006.01) | |
| A61Q 19/08 | (2006.01) | |

(Continued)

(52) U.S. Cl.
CPC ............. *C08J 3/075* (2013.01); *A61K 8/0212* (2013.01); *A61K 8/042* (2013.01); *A61K 8/45* (2013.01); *A61K 8/65* (2013.01); *A61K 8/73* (2013.01); *A61K 8/735* (2013.01); *A61K 8/736* (2013.01); *A61K 8/8152* (2013.01); *A61K 9/06* (2013.01); *A61K 31/728* (2013.01); *A61K 47/34* (2013.01); *A61K 47/36* (2013.01); *A61L 27/28* (2013.01); *A61L 27/52* (2013.01); *A61L 31/042* (2013.01); *A61L 31/145* (2013.01); *A61Q 19/00* (2013.01); *A61Q 19/02* (2013.01); *A61Q 19/08* (2013.01); *C08J 3/246* (2013.01); *C08J 3/28* (2013.01); *C12N 5/0012* (2013.01); *C12N 5/0018* (2013.01); *A61K 9/0024* (2013.01); *A61K 2800/882* (2013.01); *A61K 2800/95* (2013.01); *A61L 2430/34* (2013.01); *C08J 2305/02* (2013.01); *C08J 2305/08* (2013.01); *C08J 2333/14* (2013.01); *C08J 2371/02* (2013.01); *C08J 2389/00* (2013.01); *C12N 2500/60* (2013.01)

(58) Field of Classification Search
None
See application file for complete search history.

(56) References Cited

U.S. PATENT DOCUMENTS

| | | |
|---|---|---|
| 5,093,319 A | 3/1992 | Higham et al. |
| 5,122,614 A | 6/1992 | Zalipsky |

(Continued)

FOREIGN PATENT DOCUMENTS

| | | |
|---|---|---|
| CN | 101805465 | 8/2010 |
| CN | 102093582 | 6/2011 |
| CN | 104140541 | 11/2014 |

OTHER PUBLICATIONS

Peng et al.; Soft Matter, 2011, 7, 4881-4887. Published Apr. 8, 2011.*

(Continued)

*Primary Examiner* — Jeffrey T. Palenik
(74) *Attorney, Agent, or Firm* — Hamre, Schumann, Mueller & Larson, P.C.

(57) ABSTRACT

A method for preparing non-free radical photo-crosslinked hydrogels includes: dissolving component A that is a polymer derivative modified with o-nitrobenzyl phototrigger in a biocompatible medium to obtain solution A; dissolving component B that is a polymer derivative containing hydrazide, hydroxylamine or primary amine in a biocompatible medium to obtain solution B; mixing solution A and solution B to obtain a precursor solution of hydrogel; under light irradiation, crosslinking aldehyde generated from the o-nitrobenzyl with the hydrazine, hydroxylamine or primary amine to obtain a hydrogel by forming hydrazone, oxime or schiff base, respectively. A kit for preparation and application of the hydrogel in tissue repair, beauty therapy, and cells, proteins or drugs carriers is also described. The method or kit can achieve in situ photo-gelling on tissue surface or in situ forming thin gel on wounds in clinical treatment of wounds.

9 Claims, 5 Drawing Sheets

(51) Int. Cl.
*C08J 3/24* (2006.01)
*C12N 5/00* (2006.01)
*A61L 27/28* (2006.01)
*A61K 8/81* (2006.01)
*A61K 9/00* (2006.01)

(56) References Cited

U.S. PATENT DOCUMENTS

| | | | |
|---|---|---|---|
| 6,060,582 | A | 5/2000 | Hubbell et al. |
| 6,238,691 | B1 | 5/2001 | Huang |
| 7,070,584 | B2 | 7/2006 | Johnson et al. |
| 7,288,608 | B2 | 10/2007 | Bowman et al. |
| 2012/0149781 | A1 | 6/2012 | Lee et al. |

OTHER PUBLICATIONS

International Search Report (English and Chinese) and Written Opinion of international application No. PCT/CN2015/095260, dated Mar. 7, 2016, total 8 pages.

Oommen et al., "Smart Design of Stable Extracellular Matrix Mimetic Hydrogel: Synthesis, Characterization, and In Vitro and In Vivo Evaluation for Tissue Engineering", Advanced Functional Materials, 2013, 23, p. 1273-1280, 8 pages provided.

Jeon et al., "Biochemical and physical signal gradients in hydrogels to control stem cell behavior.", Advanced Materials, 2013, 25, p. 6366-6372, 7 pages provided.

Tong et al., "Smart chemistry in polymeric nanomedicine", Chemical Society Reviews, 2014, 43, p. 6982-7012, 31 pages provided.

Li et al., "Biodegradable and injectable in situ cross-linking chitosan-hyaluronic acid based hydrogels for postoperative adhesion prevention.", www.elsevier.com/locate/biomaterials, Biomaterials 2014, 35, p. 3903-3917, 15 pages provide.

Delaittre et al., "Acrylamide-Based Copolymers Bearing Photoreleasable Thiols for Subsequent Thiol—Ene Functionalization", Macromolecules, 2012, p. 1792-1802, 11 pages provided.

Yang et al., "Mechanical memory and dosing influence stem cell fate", Nature Materials, 2014, vol. 13, p. 645-652, 8 pages provided.

Grover et al., "Oxime Cross-Linked Injectable Hydrogels for Catheter Delivery", Advanced Materials, 2013, 25, p. 2937-2942, 6 pages provided.

* cited by examiner

PREPARATION METHOD, PRODUCT AND APPLICATION OF NON-FREE RADICAL PHOTO-CROSSLINKED HYDROGEL MATERIAL

TECHNICAL FIELD

The present invention relates to the field of biological materials. Specifically, the present invention relates to a preparation method and application of non-free radical photochemical crosslinked hydrogel materials.

BACKGROUND

Hydrogel is a kind of polymer material with high water content and three dimensional crosslinked networks. Due to the excellent biocompatibility and mechanical strength, hydrogel can highly mimic biological tissue microenvironment. Therefore, it is widely used in tissue engineering and regenerative medicine, in which tissue repairment and isolation of clinical wound is an important category. Currently, the materials used in clinic wound tissue isolation and repairment mainly include solid membrane materials (Royce Johnson et al. U.S. Pat. No. 7,070,584 B2, issued Jul. 4, 2006), preformed colloidal materials (Yeong Hua Huang et al. U.S. Pat. No. 6,238,691 B1, issued May 29, 2001), and in situ gelling materials.

Of these materials, the solid membrane materials are inconvenient to use, as they are of high cost, difficult to attach to wounds, easy to fall off from the wounds, and requires additional immobilization. In addition, the application of the solid membrane materials are seriously impacted due to lack of biodegradability. Similar to solid membrane materials, preformed colloidal materials are gelled and shaped before applying to the wound, and thus they cannot completely match the surface of the wound, which results in uncomplete coverage of the wound tissue and in turn affects their effectiveness. Compared to the above two kinds of materials, the in situ gelling materials are cured in situ on the wound. The excellent shaping property of the in situ gelling materials allows the in situ gelling materials to match the surface of the wound completely. Therefore, a good attachment to wound tissue can be achieved, which ensures good fixation and avoids falling off easily. Currently, the materials applied in in situ wound tissue isolation and repair in the market mainly include mono-component thermosensitive gel (Paul A. Higham et. al. U.S. Pat. No. 5,093,319 A, issued Mar. 3, 1992) and two-component chemical crosslinking gel (Zalipsky et. al. U.S. Pat. No. 5,122,614, issued Jun. 16, 1992). Thermosensitive gel is difficult to store and the gel strength is relatively poor. Thus its adjustable range is very narrow. For two-component chemical crosslinking hydrogel, its gelling speed is faster and gel strength is larger. Therefore, the adjustable range of this hydrogel type is wider. However, the gelling time of this materials is not controllable and the operation is inconvenient. Moreover, the instruments for mixing two-component materials are very expensive, which greatly increases the cost. Therefore, the extensive application of this kind of materials is limited.

Photoinitiated gelling materials have received widespread attention because of the advantage of non-physical contact and accurate spatiotemporal controllability of light. Traditional free radical initiated photo-polymerization (Hubbell et al. U.S. Pat. No. 6,060,582 A, issued May 9, 2000) and thiol-ene reaction developed from free radical initiated photo-polymerization (Christopher Bowman et al. U.S. Pat. No. 7,288,608 B2, issued Oct. 30, 2007) are the typical representations of photogelling reaction. In these systems, the small molecular photoinitiator must be added. The small molecular photoinitiator can generate free radicals after illumination, which in turn have great side effects on cells or biological tissue. In addition, the small molecular photoinitiator is extremely sensitive to oxygen and is difficult to prepare relatively thin layer hydrogel. However, in wound tissue isolation and repair, thin layer coating is always needed. Therefore, the traditional free radical initiated photo-polymerization is difficult to be clinically applied in in situ gelling on wounds.

In order to overcome the shortcoming of current materials, a novel non-free radical photo-crosslinking method is provided for making hydrogel. This non-free radical photo-crosslinking method not only overcomes the defects of the toxicity of free radicals and the sensitivity to oxygen, but also exhibits the characteristics of spatiotemporal controllability, simple synthesis and so on.

DETAILED DESCRIPTION

An objective of the present invention is to provide a preparation method of non-free radical photo-crosslinking hydrogel materials.

A second objective of the present invention is to provide products obtained by the preparation method of non-free radical photo-crosslinking hydrogel materials.

A third objective of the present invention is to provide applications of the products obtained by the preparation method of non-free radical photo-crosslinking hydrogel materials.

The preparation method of non-free radical photo-crosslinking hydrogel materials in this invention includes the following steps: dissolving component A (polymer derivatives modified with o-nitrobenzyl phototrigger) in biocompatible medium to obtain solution A, dissolving component B (polymer derivatives with hydrazide, hydroxylamine or primary amine) in biocompatible medium to obtain solution B; mixing solution A and solution B homogeneously to obtain precursor solution of hydrogel; under light irradiation to the above precursor solution, o-nitrobenzyl in component A after photo-activation generates aldehyde group that can crosslink with hydrazine, hydroxylamine or primary amine groups in component B to obtain hydrogel by forming hydrazone, oxime and schiff base, respectively.

The structure of component A, i.e. polymer derivatives modified with o-nitrobenzyl phototrigger, has a structural formula I:

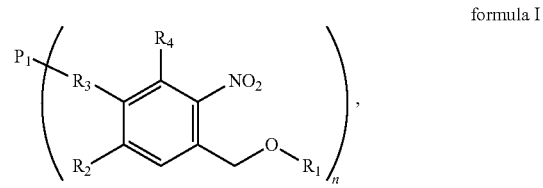

formula I where $R_1$ can be —H or substituent group as follows: ester bond such as —CO(CH$_2$)$_x$CH$_3$, —CO(CH$_2$CH$_2$O)$_x$CH$_3$, —CO(CH$_2$)$_x$(CH$_2$CH$_2$O)$_y$CH$_3$, etc., or ether bond such as —(CH$_2$)$_x$CH$_3$, —(CH$_2$CH$_2$O)$_x$CH$_3$, —(CH$_2$)$_x$(CH$_2$CH$_2$O)$_y$CH$_3$,

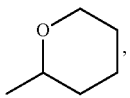

etc., or carbonic ester pond such as —COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$, etc., or carbamate bond such as —CONH(CH$_2$)$_x$CH$_3$, —CONH(CH$_2$CH$_2$O)$_x$CH$_3$, —CONH(CH$_2$)$_x$(CH$_2$CH$_2$O)$_y$CH$_3$, etc., where x and y≥0 and are integers; R$_2$ can be —H or substituent group selected as follows: —O(CH$_2$)$_x$ CH$_3$, —O(CH$_2$CH$_2$O)$_x$CH$_3$, —O(CH$_2$)$_x$(CH$_2$CH$_2$O)$_y$CH$_3$, where the x and y≥0 and are integers; R$_3$ can be selected from amino linkage bond —O(CH$_2$)$_x$CONH(CH$_2$)$_y$NH—, etc., halogenated linkage bond —O(CH$_2$)$_x$—, etc., carboxyl linkage bond —O(CH$_2$)$_x$CO—, etc., in which the ether bond is connected to the benzene ring of the molecule, and the other end is connected to polymer P$_1$, wherein the x and y≥1 and are integer; R$_4$ can be —H or substituent group such as —CONH(CH$_2$)—CH$_3$, etc., where the x≥0 and is integer; P$_1$ can be hydrophilic or water-soluble natural polysaccharide or protein and polypeptide or hydrophilic or water-soluble synthetic polymer and so on.

The structures of component B, i.e. polymer derivatives with hydrazide, hydroxylamine, primary amine, are represented by formula IIA, IIB, and IIC:

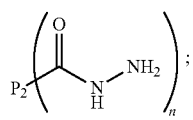

formula IIA

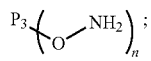

formula IIB

formula IIC where n≥2, P$_2$, P$_3$, P$_4$ are hydrophilic or water-soluble natural polysaccharide or protein and polypeptide or hydrophilic or water-soluble synthetic polymer and so on.

In the preparation method, polymer P1, i.e. the polymer derivatives modified with o-nitrobenzyl phototrigger, can be hydrophilic or water-soluble natural polymer, for examples, the natural polysaccharide (such as hyaluronic acid, heparin, alginate, dextran, carboxymethyl cellulose, glycol chitosan, propylene glycol chitosan, chitosan lactate, carboxymethyl chitosan, chitosan quaternary ammonium salt, etc.) and their modified or degradative products; protein or peptide, for examples, all kinds of hydrophilic or water-soluble plant and animal protein, collagen, serum protein, gelatin and their modified or degradative peptide; hydrophilic or water-soluble synthetic polymer, for examples, two or multi-arms polyethylene glycol, polyethyleneimine, dendrimer, synthetic peptide, polylysine and (methyl) acrylate or (methyl) acrylamide polymer, etc. In the above hydrophilic or water-soluble polymers, the average number of o-nitrobenzyl phototrigger in single polymeric molecule is greater than or equal to 2 (degree of functionality n≥2). In addition, the polymer derivatives modified with o-nitrobenzyl phototrigger can be hydrophilic or water-soluble polymer with one or more different groups, or a mixture of hydrophilic or water-soluble polymer with one or more different groups.

In the preparation method of the present invention, of the structures of polymer derivatives with hydrazide, hydroxylamine, primary amine, P$_2$—(CO—NH—NH$_2$)$_n$ represents hydrophilic or water-soluble polymer containing multi hydrazide groups (n≥2). The P$_2$ polymer can be natural polysaccharide (for examples, dextran, hyaluronic acid, heparin, alginate, carboxymethyl cellulose, glycol chitosan, propylene glycol chitosan, chitosan lactate, carboxymethyl chitosan, chitosan quaternary ammonium salt, etc.) and its modified or degradative products; protein or peptide (for examples, all kinds of hydrophilic or water-soluble plant and animal protein, collagen, serum protein, gelatin, etc.) and their modified or degradative peptides; hydrophilic or water-soluble synthetic polymer, for examples, polyethylene glycol (for example, polyethylene glycol having two or multi arms), polyethyleneimine, dendrimer, synthetic peptide, polylysine, (methyl) acrylate polymer, (methyl) acrylamide polymer, or their modifications. P$_3$—(O—NH$_2$)$_n$ represents hydrophilic or water-soluble polymer containing multi hydroxyamino groups (n≥2). The P$_3$ polymer can be natural polysaccharide (such as dextran, hyaluronic acid, heparin, alginate, carboxymethyl cellulose, glycol chitosan, propylene glycol chitosan, chitosan lactate, carboxymethyl chitosan, chitosan quaternary ammonium salt, etc.) and their modified or degradative products; also can be protein or peptide (such as hydrophilic or water-soluble plant and animal protein, collagen, serum protein, gelatin, etc.) and their modified or degradative peptides; also can be hydrophilic or water-soluble synthetic copolymer, such as two or multi-arms polyethylene glycol, polyethyleneimine, dendrimer, synthetic peptide, polylysine and (methyl) acrylate or (methyl) acrylamide polymer and their modifications. P$_4$—(NH$_2$)$_n$ represents hydrophilic or water-soluble polymer containing multi amino groups (n≥2). The P4 polymer can be synthetic polyamine polymer and their modifications (such as polyethyleneimine, dendrimer, polyethylene glycol having two or multi arms), or natural polysaccharide of hydrophilic or water-soluble polymer and their modified or degradative products containing amino group (such as glycol chitosan, propylene glycol chitosan, chitosan lactate, chitosan quaternary ammonium salt, carboxymethyl chitosan, oligochitosan, etc.); also can be protein and peptide (such as hydrophilic or water-soluble plant and animal protein, collagen, serum protein, gelatin) and their modified or degradative peptides; also can be hydrophilic or water-soluble synthetic polymer, such as two or multi-arms polyethylene glycol, polyethyleneimine, dendrimer, synthetic peptide, polylysine and (methyl) acrylate or (methyl) acrylamide polymer and their modifications. In addition, the polymer derivatives with hydrazide, hydroxylamine, primary amine can be hydrophilic or water-soluble polymer with one or more different groups, or mixture of hydrophilic or water-soluble polymer with one or more different groups.

In the preparation method of the present invention, the biocompatible medium can be selected from distilled water, saline, buffer and cell culture medium solution. According to different application, different medium can be chosen.

In the preparation method of the present invention, in the hydrogel precursor mixture of solution A and solution B, the molar ratio of the o-nitrobenzyl group to hydrazine/hydroxylamine/primary amine group can be from 1:0.02 to 1:50, preferably from 1:0.1 to 1:10; total concentration of polymer can be from 0.1 wt % to 60 wt %, preferably from 1 wt % to 10 wt %.

In the preparation method of the present invention, the illumination wavelength is determined according to the absorption of o-nitrobenzyl phototrigger, which can be from 250 nm to 500 nm, preferably from 300 nm to 400 nm, more preferably 365 nm.

FIG. 1 illustrates of the technology principle of the preparation method in accordance with some embodiments. Referring to FIG. 1, o-nitrobenzyl phototrigger generates aldehyde group after photo-activation, which quickly cross-links with hydrazine, hydroxylamine, or primary amine group of a polymer to obtain hydrogel by forming hydrazone, oxime and schiff base, respectively. —$R_5$—$NH_2$ of the polymer can be —$CONHNH_2$, —O—$NH_2$ or —$NH_2$.

In this invention, the preparation methods of polymer derivatives modified with o-nitrobenzyl include chemical grafting method and artificial polymerization method. The chemical grafting method utilizes chemical reaction of chemical groups between polymer and o-nitrobenzyl derivatives, such as the reaction between carboxyl polymer and o-nitrobenzyl molecular containing amino group (O. P. Oommen, S. Wang, M. Kisiel, M. Sloff, J. Hilborn, O. P. Varghese, *Adv. Funct. Mater.* 2013, 23, 1273.), or the reaction between hydroxyl polymer and o-nitrobenzyl molecular containing carboxyl or bromated group (K. Peng, I. Tomatsu, A. V. Korobko, A. Kros, *Soft Matter* 2010, 6, 85; L. Li, N. Wang, X. Jin, R. Deng, S. Nie, L. Sun, Q. Wu, Y. Wei, C. Gong, Biomaterials 2014, 35, 3903.), or the reaction between amino polymer and o-nitrobenzyl molecular containing bromated group (L. Li, N. Wang, X. Jin, R. Deng, S. Nie, L. Sun, Q. Wu, Y. Wei, C. Gong, *Biomaterials* 2014, 35, 3903.) and so on. The artificial polymerization method utilizes copolymerization of o-nitrobenzyl derivatives containing functional monomer with other monomers, which can be random free radical polymerization, or controllable radical polymerization method (such as ATRP polymerization and RAFT polymerization) and so on.

In this invention, the preparation method of polyethylene glycol or natural polysaccharide polymer derivatives modified with o-nitrobenzyl is as follows: water-soluble polymer or macromolecule containing carboxyl group was dissolved in distilled water and o-nitrobenzyl molecule containing active amino functional group was added; Following by adding the condensing agent 1-ethyl-(3-dimethyl amino propyl) carbodiimide hydrochloride (EDC-HCl) and activator hydroxyl benzotriazole (HOBt), the above solution was then stirred for 24-48 h at room temperature. After the reaction, the mixture is dialyzed for 2-3 d against diluted hydrochloric acid solution and then freeze-dried into the polymer derivatives modified with o-nitrobenzyl.

The water-soluble polymer or macromolecule containing carboxyl group described above can be polyethylene glycol and polysaccharide containing carboxyl group (such as hyaluronic acid, carboxymethyl cellulose, alginate, etc.), preferably multi-arms carboxyl polyethylene glycol, hyaluronic acid and carboxymethyl cellulose, more preferably hyaluronic acid.

In this invention, the preparation method of polyethylene glycol or natural polysaccharide polymer derivatives modified with o-nitrobenzyl is as follows: water-soluble polymer containing hydroxyl group was dissolved in distilled water, following by adding a small o-nitrobenzyl derivative molecule containing active carboxyl functional group. Thereafter, the condensing agent 1-ethyl-(3-dimethyl amino propyl) carbodiimide hydrochloride (EDC-HCl) and the catalyst p-toluene sulfonic acid pyridine salt (DPTS) are added. The resulted mixture was then stirred for 24-48 h at room temperature. After the reaction is completed, the mixture is poured into insoluble solvent for precipitation (for example, the modified polyethylene glycol derivatives can be poured into the ether for precipitation and polysaccharide polymer derivatives can be poured into the ethanol for precipitation), dissolved in water to dialyze for 2-3 d, and then freeze-dried into the polymer derivatives modified with o-nitrobenzyl.

The water-soluble polymer containing hydroxyl group described above can be polyethylene glycol or natural polysaccharide, preferably multi-arms polyethylene glycol and dextran, more preferably dextran.

In this invention, the preparation method of polyethylene glycol or natural polysaccharide polymer derivatives modified with o-nitrobenzyl is as follows: water-soluble polymer containing amino or hydroxyl group was dissolved in distilled water and o-nitrobenzyl molecule containing active bromated functional groups was added. Following by adding potassium carbonate as alkali, the resulted mixture was then reacted for 24-48 h at room temperature. After the reaction, the mixture is poured into insoluble solvent for precipitation (for example, the modified polyethylene glycol derivatives can be poured into the ether, and the modified polysaccharide polymer derivatives can be poured into the ethanol), dissolved in water to dialyze for 2-3 d, and then freeze-dried into the polymer derivatives modified with o-nitrobenzyl.

The water-soluble polymer containing amino or hydroxyl group described above can be polyethylene glycol, natural polysaccharide containing amino or hydroxyl, preferably multi-arms amino polyethylene glycol, multi-arms hydroxyl polyethylene glycol, glycol chitosan, propylene glycol chitosan, carboxymethyl chitosan, chitosan lactate, and natural polysaccharide, more preferably glycol chitosan and multi-arms hydroxyl polyethylene glycol.

In the above reaction, the molar ratio of carboxyl, amino or hydroxyl group of the water-soluble polymer to the small o-nitrobenzyl derivative molecule is preferably from 1:0.1 to 1:2. The molar ratio of the small o-nitrobenzyl molecule modified with amino group to 1-ethyl-(3-dimethyl amino propyl) carbodiimide hydrochloride (EDC-HCl) to the activator hydroxyl benzotriazole (HOBt) is preferably 1:2:1.5. The molar ratio of the small o-nitrobenzyl molecule modified with carboxyl group to 1-ethyl-(3-dimethyl amino propyl) carbodiimide hydrochloride (EDC-HCl) to the catalyst DPTS is preferably 1:2:1.5. The molar ratio of the small o-nitrobenzyl molecule modified with bromated group to potassium carbonate is preferably 1:2.

In this invention, the preparation method of the synthetic copolymer modified with o-nitrobenzyl is as follows: copolymerizing polymerizable o-nitrobenzyl monomer derivatives with one or more polymerizable monomer to obtain a synthetic copolymer modified with o-nitrobenzyl. The synthetic copolymer can be purified through cycles of dissolution—precipitation method.

The polymerizable o-nitrobenzyl monomer derivatives described above can contain (methyl) acrylate or (methyl) acrylamide, preferably methyl acrylate and acrylamide, more preferably methyl acrylate.

At least one of the above polymerizable monomers is water-soluble monomer, which can be polyethylene glycol methacrylate (PEG-MA), polyethylene glycol acrylate, methyl acrylic acid (MAA), acrylic acid (AA), hydroxyl ethyl acrylate, acrylamide (AM), and any other water-soluble polymerizable monomer, preferably polyethylene glycol methacrylate (PEG-MA). The selection of the polymerizable monomers is dependent on the specific application.

The molar ratio of the polymerizable o-nitrobenzyl monomer derivatives to the water-soluble monomer can be 1:20-1:2, preferably 1:9-1:3, and more preferably 1:4.

The polymerization methods described above can be random free radical polymerization, or controllable radical polymerization (such as RAFT polymerization, ATRP polymerization and so on). The optimal mothed is random free radical polymerization. Namely, the polymerizable o-nitrobenzyl monomer derivatives and co-monomer were dissolved in certain solvent and free radical initiator was added and dissolves adequately. After three times of frozen-vacuum cyclic operation, the mixture was heated and reacts overnight. At the end of reaction, the mixture was poured into anhydrous diethyl ether for precipitation. After purification by manifold cycles of dissolution—precipitation and further drying under vacuum, the copolymer modified with o-nitrobenzyl was obtained. (G. Delaittre, T. Pauloehrl, M. Bastmeyer, C. Barner-Kowollik, *Macromolecules* 2012, 45, 1792-1802.)

In this invention, the preparation method of the polymer derivatives modified with hydrazide is described as follows. Water-soluble polymer containing carboxyl group and di-hydrazide were dissolved in distilled water. The condensing agent of 1-ethyl-(3-dimethyl amino propyl) carbodiimide hydrochloride (EDC-HCl) and activator of hydroxyl benzotriazole (HOBt) were added. The resulted mixture was then stirred for 24-48 h at room temperature. After the reaction, the mixture is dialyzed for 2-3 d against dilute hydrochloric acid solution and then freeze-dried into the polymer derivatives modified with hydrazide.

The water-soluble polymer containing carboxyl group described above can be carboxyl polyethylene glycol and polysaccharide containing carboxyl group (such as chitosan lactate, carboxymethyl chitosan, hyaluronic acid, alginate and carboxymethyl cellulose, etc.), preferably multi-arms carboxyl polyethylene glycol, hyaluronic acid, more preferably hyaluronic acid.

In the above reaction, di-hydrazide molecule can be carbodihydrazide, oxalic acid dihydrazide, malonic acid dihydrazide and succinic acid dihydrazide, glutaric acid dihydrazide, adipic acid dihydrazide, pimelic acid dihydrazide and other dihydrazide, preferably carbodihydrazide, oxalic acid dihydrazide and adipic acid dihydrazide, more preferably carbodihydrazide. The molar ratio of carboxyl group in water-soluble polymer to dihydrazide molecule is preferably 1:0.1-2. The molar ratio of dihydrazide molecule, 1-ethyl-(3-dimethyl amino propyl) carbodiimide hydrochloride (EDC-HCl), and the activator hydroxyl benzotriazole (HOBt) is preferably 1:2:1.5.

In this invention, the preparation method of polymer derivatives modified with hydroxylamine is described as follows. Polymer containing hydroxyl group and N-hydroxyl phthalimide were dissolved in dichloromethane. After adding triphenylphosphine, diisopropyl azo dicarboxylic acid ester was added slowly and the resulted mixture was reacted for 16-24 h. The polymer was precipitated in the ether and re-dissolve in dichloromethane. Hydrazine hydrate was added to the above solution and reacted for 1-3 h to obtain polymer derivatives modified with hydroxylamine.

The polymer containing hydroxyl group described above can be polyethylene glycol or polysaccharide (such as dextran and chitosan), preferably multi-arms hydroxyl polyethylene glycol.

In the above reaction, the molar ratio of the hydroxyl group in polymer, N-hydroxyl phthalimide, triphenylphosphine, diisopropyl azo dicarboxylic acid ester and hydrazine hydrate is preferably 1:10:10:10:10.

In this invention, the water-soluble polymers modified with amino group can be artificial synthetic polyamine polymer and their modifications (such as polyethyleneimine PEI, dendrimer PAMAM and two or multi-arms amino polyethylene glycol), or can be hydrophilic or water-soluble polysaccharide polymer naturally containing amino group and their modified or degradative products (such as glycol chitosan, propylene glycol chitosan, chitosan lactate, carboxymethyl chitosan, and oligochitosan, etc.); or can be protein and their modified and degradative products after extraction of creature or microorganism expression (such as collagen, serum protein, and gelatin, etc.); or can be hydrophilic or water-soluble polypeptide containing two or more than two amino groups, which was obtained through chemical synthesis or microorganism expression and extraction (such as polylysine, etc.), (methyl) acrylate, or (methyl) acrylamide polymers and their modifications. preferably is gelatin and glycol chitosan.

The present invention provides a kind of hydrogel prepared by the method arising in this invention, which can be named non-free radical photochemical crosslinking hydrogel.

The present invention further provides a kit for preparing hydrogel using the disclosed method, which includes component A (polymer derivatives modified with o-nitrobenzyl phototrigger shown as Structure formula I), component B (polymer derivatives with hydrazide, hydroxylamine or primary amine shown as Structure IIA, IIB, IIC), and instructions of the preparation and application of the hydrogel.

The kit can further include biocompatible medium, such as buffer and cell culture medium.

The instructions of the kit describe the applications of hydrogel including the applications in tissue repair, beauty, and cells, proteins, or drugs carrier.

The invention relates to application of the aforementioned non-free radical photochemical crosslinking hydrogel for wound tissue repair—skin wound healing.

The invention also relates to application of the aforementioned non-free radical photochemical crosslinking hydrogel for wound tissue isolation—postsurgical anti-adhesion.

The invention also relates to application of the aforementioned non-free radical photochemical crosslinking hydrogel for cells, proteins, or drugs carrier.

The invention also relates to application of the aforementioned non-free radical photochemical crosslinking hydrogel for beauty.

Comparing with the current technology, the present invention has the following innovative points:

(1) The present invention discloses a new preparation method of photochemical crosslinking hydrogel materials. Compared with thermochemical crosslinking method, preformed gel and solid film. The mothed of photo crosslinking has the advantages of precise spatiotemporal controllability and convenient operation.

(2) The raw material source in this present invention is wide available. The preparation process of the hydrogel is simple and the cost of application is low. According to the needs for different applications, the chemical structure, composition, strength, thickness and other character of the hydrogel can be flexibly adjusted. Thus, the hydrogel is widely applicable.

(3) The crosslinking mechanism of the photochemical crosslinking hydrogel described in this present invention is non-free radical crosslinking mechanism, which can effectively overcome the defects of biological toxicity and oxygen inhibition of traditional free radicals crosslinking mechanism.

(4) The technology in this present invention can be conducted in situ on tissue surface, which has the advantages of convenient operation, in situ molding, excellent adhesion to biological tissue and so on.

(5) The chemical structure, composition, degradability, strength and thickness of the hydrogel are adjustable, which means the properties of the gel materials can be adjusted flexibly according to different applications. The property of forming thin gel in situ on wounds is particularly suitable for the clinical treatment of tissue isolation and repair. Meanwhile, the method can also provide in situ forming cells or proteins carrier, which can be effectively applied in tissue engineering and regenerative medicine.

EXAMPLES

Figure 1:
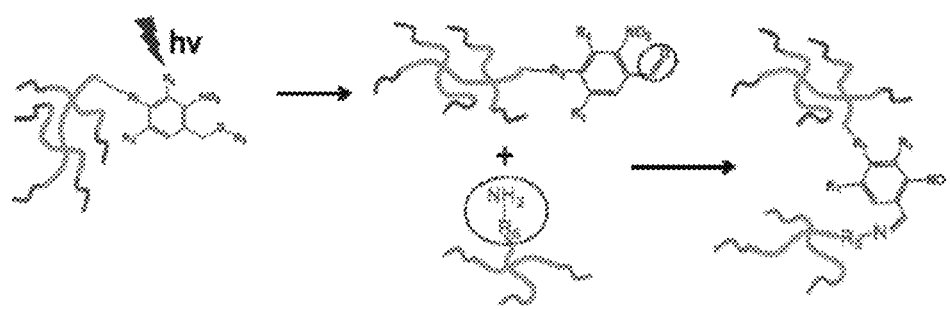
FIG. 1 illustrates a crosslink of o-nitrobenzyl phototrigger with a polymer containing with hydrazine, hydroxylamine, or primary amine group, in accordance with some embodiments.

The following exemplary embodiments will provide more detailed description to this invention. The invention will be further described by combining with appended figures and exemplary embodiments. These examples are just for illustrating embodiments of the invention, but are not intended to limit the scope of this invention. Any other variations and modifications made by inventors abiding the spirit of invention and protection are still within the protection of this invention.

Exemplary Embodiment 1: Synthesis of o-Nitrobenzyl (HA-NB) Modified Hyaluronic Acid Derivative

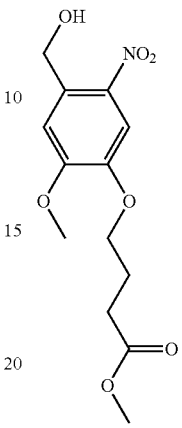

Compound 1

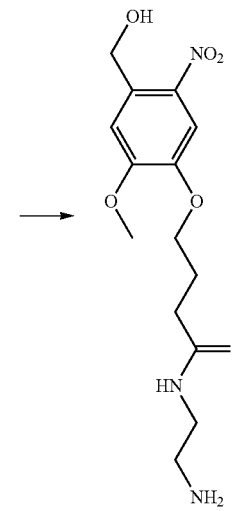

Compound 2

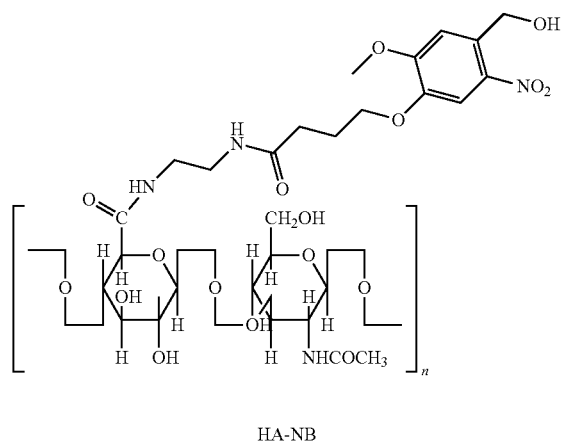

HA-NB (1) Synthesis of Compound 1:

compound 1 was synthesized according to a method reported in Pauloehrl, T.; Delaittre, G.; Bruns, M.; Meißler, M.; Borne; H. G.; Bastmeyer, M.; Barner-Kowollik, C. Angew. *Chem. Int. Ed.* 2012, 51, 9181.

(2) Synthesis of Compound 2:

compound 1 (1 g, 3.3 mmol) and ethylenediamine (1.1 mL) were dissolved in methanol (50 mL). The mixture was refluxed overnight. After that, the solvent was evaporated in vacuum to obtain crude product. The crude product was dissolved in methanol and precipitated in ethyl acetate. After several times of dissolution-precipitation, filtration, vacuum drying, the pure compound 2 (0.93 g, yield 85%) was obtained.

(3) Synthesis of HA-NB:

hyaluronic acid HA (400 mg) was dissolved in 50 mL distilled water and hydroxyl benzotriazole (HOBt, 153 mg) was added. Then the methanol solution of compound 2 (224 mg, 0.69 mmol) and 1-ethyl-(3-dimethyl amino propyl) carbodiimide hydrochloride (EDC-HCl, 200 mg) was added into the above solution. After stirring for 48 h at room temperature, the solution was firstly dialyzed against diluted HCl (pH=3.5) containing NaCl for 1 d, then dialyzed against purified water for 1 d. The solution was lyophilized to obtain HA-NB (410 mg) solid. The substitution degree of o-nitrobenzyl group was calculated according to the result of $^1$H NMR as 7%.

Exemplary Embodiment 2: Synthesis of o-Nitrobenzyl Modified Dextran Derivative (Dextran-NB)

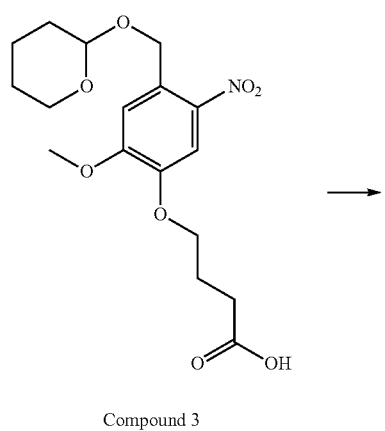

Compound 3

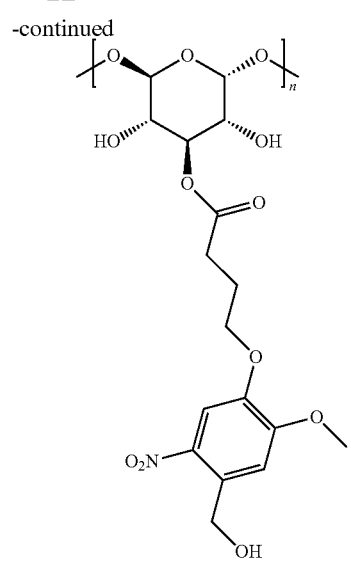

Dextran-NB (1) Synthesis of Compound 3:

it was synthesized according to the public method in the reference Pauloehrl, T.; Delaittre, G.; Bruns, M.; Meißer, M.; Börner, H. G.; Bastmeyer, M.; Barner-Kowollik, C. Angew. Chem. Int. Ed. 2012, 51, 9181.

(2) Synthesis of Dextran-NB:

1 g dried dextran was dissolved in dry DMSO. Compound 3 (0.23 g, 0.62 mmol), EDC-HCl (0.76 g, 3.96 mmol) and DPTS (0.12 g) were added sequentially to the above dextran solution followed by stirring for 48 h at room temperature. After completed reaction, the solution was poured into cold ethanol for precipitation and purified by three times of dissolution-precipitation and dried in vacuum to get pure dextran-NB (0.8 g). The substitution degree of o-nitrobenzyl group was calculated according to the result of $^1$H NMR as approximate 10%.

Exemplary Embodiment 3: Synthesis of o-Nitrobenzyl Modified Chitosan Derivative (Chitosan-NB)

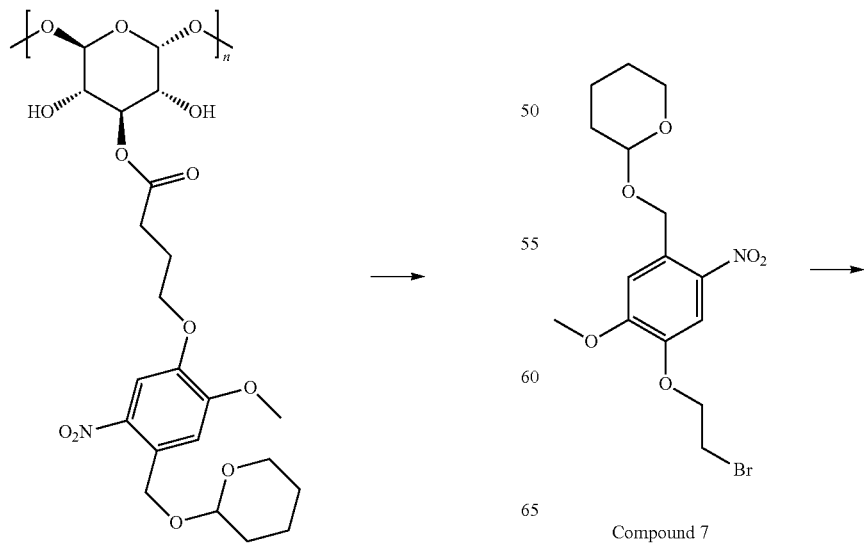

Compound 7

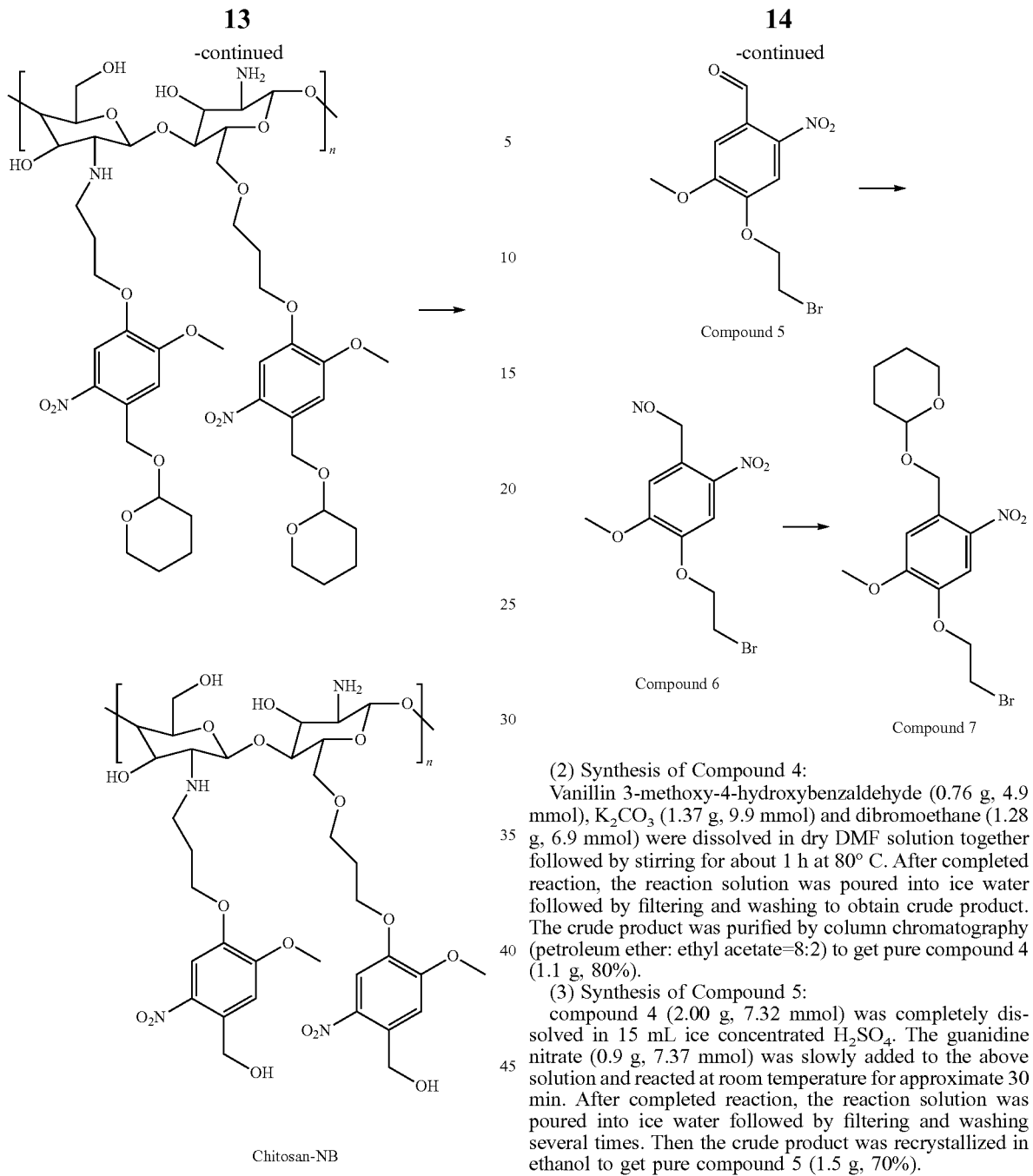

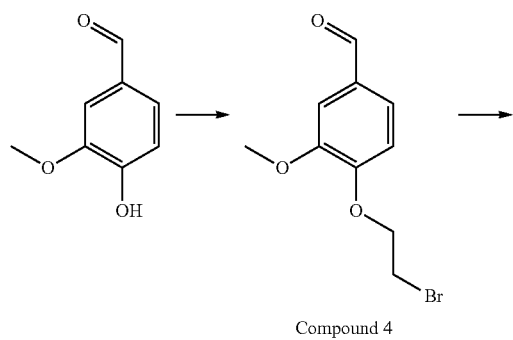

Compound 4

Compound 5

Compound 6

Compound 7

Chitosan-NB (1) Synthesis of Bromated o-Nitrobenzyl Molecule:

(2) Synthesis of Compound 4:

Vanillin 3-methoxy-4-hydroxybenzaldehyde (0.76 g, 4.9 mmol), $K_2CO_3$ (1.37 g, 9.9 mmol) and dibromoethane (1.28 g, 6.9 mmol) were dissolved in dry DMF solution together followed by stirring for about 1 h at 80° C. After completed reaction, the reaction solution was poured into ice water followed by filtering and washing to obtain crude product. The crude product was purified by column chromatography (petroleum ether: ethyl acetate=8:2) to get pure compound 4 (1.1 g, 80%).

(3) Synthesis of Compound 5:

compound 4 (2.00 g, 7.32 mmol) was completely dissolved in 15 mL ice concentrated $H_2SO_4$. The guanidine nitrate (0.9 g, 7.37 mmol) was slowly added to the above solution and reacted at room temperature for approximate 30 min. After completed reaction, the reaction solution was poured into ice water followed by filtering and washing several times. Then the crude product was recrystallized in ethanol to get pure compound 5 (1.5 g, 70%).

(4) Synthesis of Compound 6:

compound 5 (2.58 g, 8.5 mmol) was dissolved in methanol and $NaBH_4$ (0.48 g, 12.75 mmol) was slowly added. After reacting at room temperature for 2 h, the solvent was evaporated in vacuum and purified by column chromatography (EA:PE=5:1) to get pure compound 6 (2.28 g, 88%).

(5) Synthesis of Compound 7:

compound 6 (0.88 g, 2.9 mmol) was dissolved in dichloromethane. 3,4-dihydro-2H-pyran (0.365 g, 4.3 mmol) and pyridine hydrochloride (72 mg, 0.6 mmol) were added sequentially. After reacting at room temperature for approximate 2 h, the solvent was evaporated in vacuum and recrystallized in diethyl ether to get pure compound 7 (0.73 g, 65%).

(6) Synthesis of Chitosan-NB:

10 g chitosan was added to 75 mL isopropanol to form a suspension. 25 mL NaOH solution (10 mol/L) was slowly added to the above suspension of chitosan in five times and the mixture was stirred for 0.5 h. Then compound 7 (20 g)

was added to the above solution. After reacting at 60° C. for 3 h, the mixture solution was filtered and the filtrate was dialyzed three times with mixed solvent of methanol/water, and dialyzed twice in methanol, then lyophilized to get compound 7 modified chitosan (9.1 g). The compound 7 modified chitosan was dissolved in DMSO followed by adding p-toluenesulfonic acid to deprotect dihydropyran to get Chitosan-NB. The substitution degree of o-nitrobenzyl group was calculated according to the result of $^1$H NMR as approximate 9%.

Exemplary Embodiment 4: Synthesis of o-Nitrobenzyl Modified Polyethylene Glycol Derivative (PEG-4NB)

PEG-4OH (1 g, 0.05 mmol) was dissolved in anhydrous acetonitrile followed by adding $K_2CO_3$ (55.3 mg, 0.4 mmol). The solution was stirred for 30 min. Then, compound 7 (0.16 g, 0.4 mmol) was added to react for 24 h at room temperature. After completed reaction, most of the solvent was removed and the residual solution was precipitated in the ether. The precipitates were filtrated, washed and dried to get PEG-4NB (1.1 g). The substitution degree of o-nitrobenzyl group was calculated according to the result of $^1$H NMR as approximate 95%.

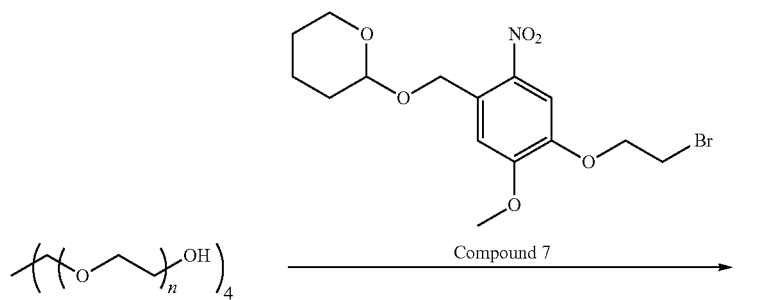

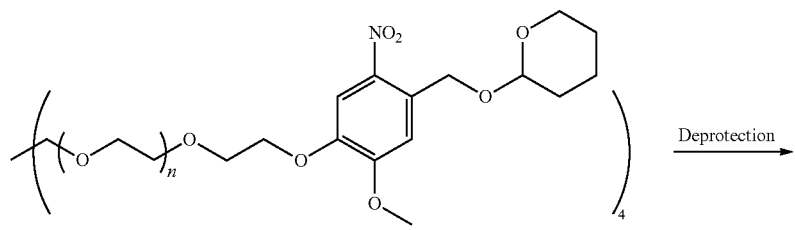

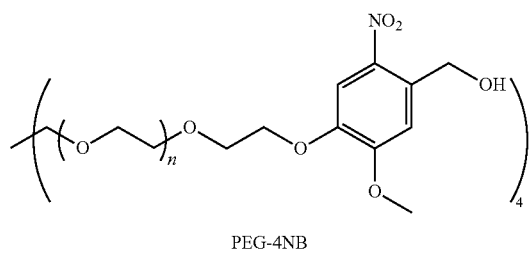

PEG-4NB

Exemplary Embodiment 5: Synthesis of o-Nitrobenzyl Modified Synthetic Copolymer (Copolymer-NB)
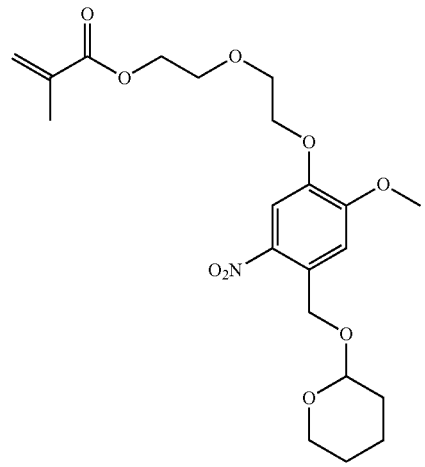
Compound 9
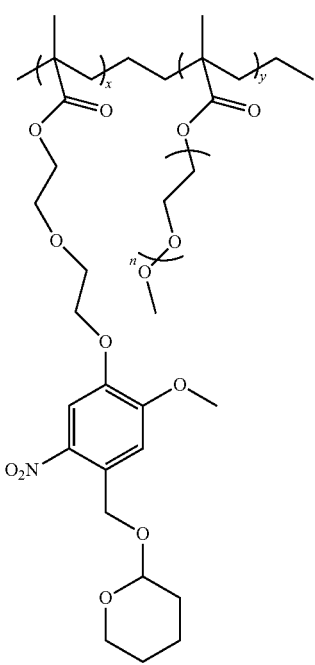
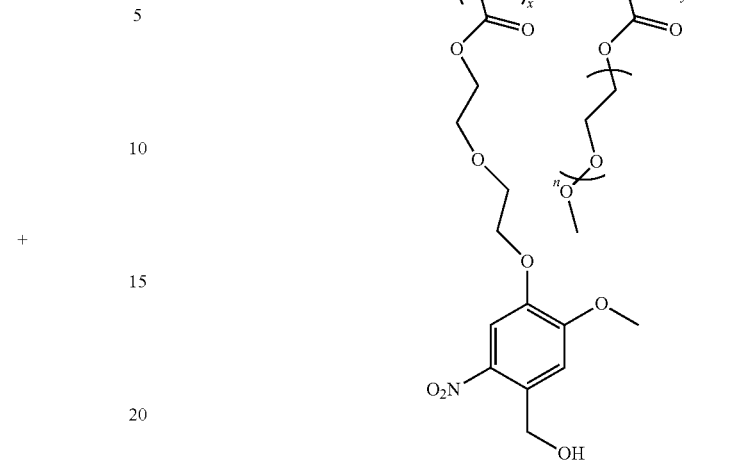
Copolymer-NB
(1) Synthesis of o-Nitrobenzyl Methyl Acrylate Monomer:
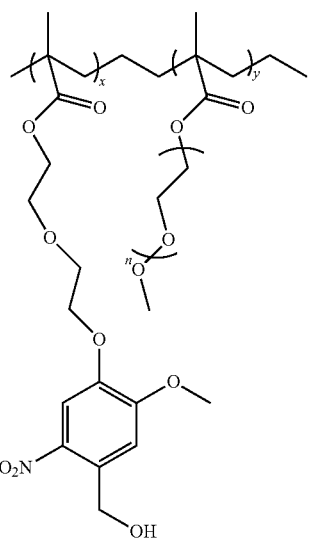
Compound 7
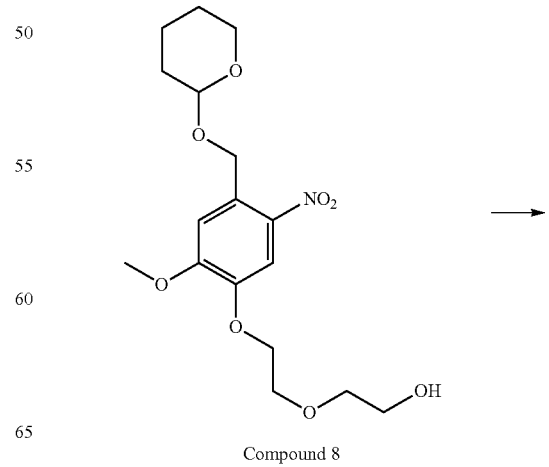
Compound 8

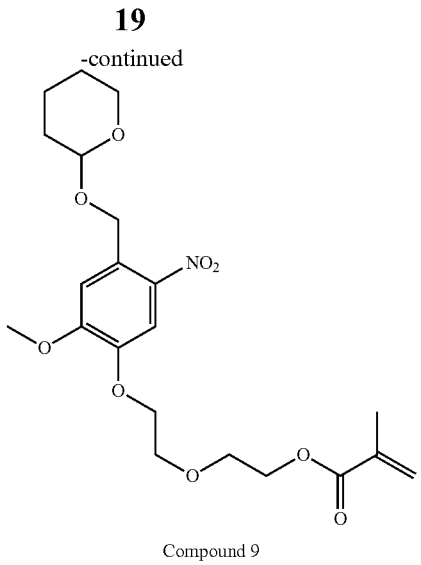

Compound 9

(2) Synthesis of Compound 8:

compound 7 (0.5 g, 1.29 mmol) and ethylene glycol (0.24 g, 3.87 mmol) were dissolved in anhydrous acetonitrile and $K_2CO_3$ (0.5 g, 3.87 mmol) was added as alkali. Then the mixture was refluxed overnight. After completed reaction, the solvent was evaporated in vacuum and purified by column chromatography to get pure compound 8 (0.34 g, 72%).

(3) Synthesis of Compound 9:

compound 8 (0.64 g, 1.72 mmol) and triethylamine (0.34 g, 3.44 mmol) were dissolved in dry dichloromethane and methyl acryloyl chloride (0.27 g, 2.58 mmol) was slowly dropped to the above solution incubated in ice bath. After reacting overnight at room temperature, the solvent was evaporated in vacuum and the crude product was purified by column chromatography to get pure compound 9 (0.49 g, 65%).

(4) Synthesis of Copolymer-NB:

compound 9 (0.28 g, 0.63 mmol), comonomer PEG-MA (0.882 g, 2.52 mmol) and initiator azodiisobutyronitrile (11 mg) were added into Shrek tube and anhydrous THF was added to dissolve them. After several times of frozen-vacuum cyclic operation, the system reacted under the condition of 75° C. for 24 h., Then the reaction solution was poured into cold ether and washed with cold ether for three times. The collected precipitation was dried and dissolved in anhydrous DMSO, and p-toluene sulfonic acid was added to deprotect dihydrogen pyran group to get copolymer-NB (0.8 g). The graft ratio of o-nitrobenzyl group in copolymer was calculated according to the result of $^1H$ NMR as approximate 17%.

Exemplary Embodiment 6: Synthesis of Carbodihydrazide Modified Hyaluronic Acid Derivatives (HA-CONHNH$_2$, HA-CDH)

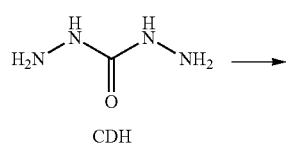

CDH

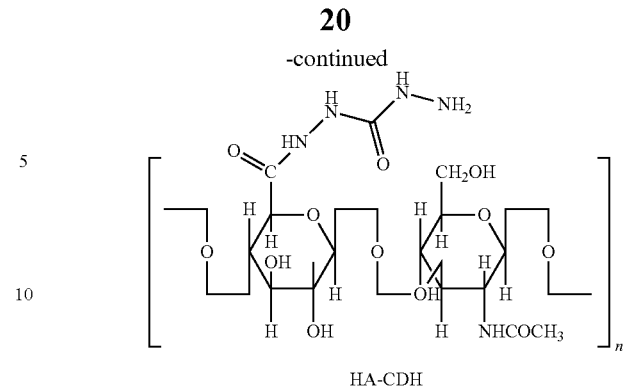

HA-CDH

Hyaluronic acid HA (400 mg) was completely dissolved in 50 mL distilled water. Hydroxyl benzotriazole (HOBt, 153 mg), carbodihydrazide (CDH, 90 mg), 1-ethyl-(3-dimethylaminopropyl) carbodiimide hydrochloride (EDC-HCl, 90 mg) were added to the above solution. After reacting at room temperature for 48 h, the solution was dialyzed against diluted HCl solution (pH=3.5) containing NaCl for 1 d, and then dialyzed against purified water for 1 d. The solution was lyophilized to obtain HA-CDH (410 mg). The product was characterized using TNBS assay as reporting in the following reference. [Oommen, O. P.; Wang, S.; Kisiel, M.; Sloff, M.; Hilborn, J.; Varghese, O. P. *Adv. Funct. Mater.* 2013, 23, 1273]. The modified degree of carbodihydrazide in the final product is approximate 6%.

Exemplary Embodiment 7: Synthesis of Hyaluronic Acid Derivatives Modified with Oxalic Acid Dihydrazide (HA-ODH)

According to the method in Exemplary Embodiment 6, HA-ODH was synthetized using the raw materials of hyaluronic acid, hydroxyl benzotriazole, oxalic acid dihydrazide and 1-ethyl-(3-dimethylaminopropyl) carbodiimide hydrochloride. The grafting degree of HA-ODH is approximate 8% according to TNBS assay.

Exemplary Embodiment 8: Synthesis of Adipic Acid Dihydrazide Modified Hyaluronic Acid Derivative (HA-ADH)

According to the method in Exemplary Embodiment 6, HA-ADH was synthetized using hyaluronic acid, hydroxyl benzotriazole, adipic acid dihydrazide and 1-ethyl-(3-dimethylaminopropyl) carbodiimide hydrochloride. The grafting degree of HA-ADH is approximate 6% according to the result of TNBS assay.

Exemplary Embodiment 9: Synthesis of Hydroxylamine Modified Four-Arm Polyethylene Glycol Derivative

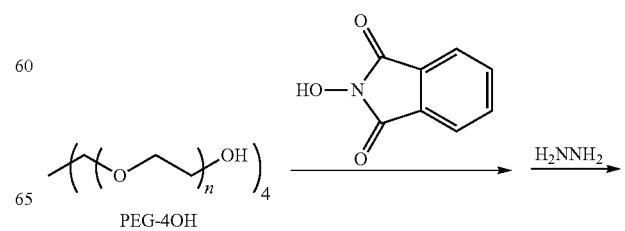

PEG-4OH

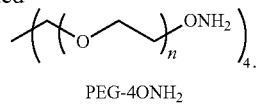

PEG-4ONH$_2$

The synthetic procedure of hydroxylamine modified four-arm polyethylene glycol derivative was based on the public method in the following reference [Grover, G. N.; Braden, R. L.; Christman, K. L. Adv. Mater. 2013, 25, 2937.]. Briefly, four arm polyethylene glycol (PEG-4OH, 2 g, 97.3 μmol) and N-hydroxyl phthalimide (634.6 mg, 3.89 mmol) were dissolved in dry dichloromethane. Then, triphenylphosphine (1.02 g, 3.89 mmol) was added slowly to the above solution incubated in ice bath followed by further reacting for approximately 30 min. Then, diisopropyl azodicarboxylate (765.9 μL, 3.89 mmol) was dissolved in dry dichloromethane and dropped slowly into the above solution. The solution reacted at temperature for 1 d, after which the solution was poured into ether and the participated solid was filtered. The product (0.25 g, 11.8 μmop was redissolved in acetonitrile again and hydrazine monohydrate (22.9 μL, 473 μmol) was added. After stirring for 2 h. dichloromethane was added to the mixture solution followed by filtering through diatomite. The obtained liquid was evaporated in vacuum to get hydroxylamine modified four-arm polyethylene glycol (PEG-4ONH$_2$).

Exemplary Embodiment 10: Synthesis of Hydroxylamine Modified Dextran Derivatives According to the method in Exemplary Embodiment 9, the dextran modified with hydroxylamine was synthetized using dextran, N-hydroxyl phthalimide, triphenylphosphine, diisopropyl azodicarboxy late, hydrazine monohydrate.

Exemplary Embodiment 11: Hydrogel Preparation by the Non-Free Radical Photo-Crosslinking Gelation According to the method of the present invention, different hydrogel precursor solutions were prepared at 37° C. with the composition of A:B=1:1 (w/w) as shown in Table 1.

Figure 2:
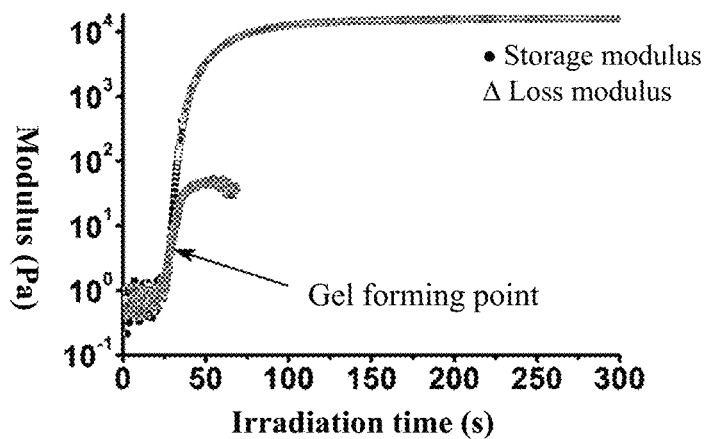
FIG. 2 is the dynamic rheological curve of 10% wt hydrogel precursor solution (copolymer-NB+PEG-4ONH$_2$) under light irradiation.

Exemplary Embodiment 12: Rheological Analysis of the Non-Free Radical Photocrosslinking Hydrogel Rheological analysis was conducted by rheometer AR2000ex (TA). The rheological test was carried out at 37° C. testing platform (φ=20 mm). In this exemplary embodiment, the relationship between the storage modulus of the hydrogels and irradiation time or polymer concentration was investigated. FIG. 2 shows the gelation curve of the precursor solution containing 10% wt copolymer-NB (Exemplary Embodiment 5) and PEG-4ONH$_2$ with equal mass ratio (Exemplary Embodiment 7) under irradiation FIG. 2 showed the hydrogel precursor solution gelled at about 30 s after light irradiation and approached the final modulus of $10^4$ Pa at about 100 s after light irradiation. In addition, the gel strength is proportional to polymer concentration, in which the hydrogel with higher polymer concentration exhibits lager gel strength. The gelation point and gel strength of the hydrogels composed with other polymers are shown in Table 2.

TABLE 2

| Composition of hydrogel materials (A/B) | Gel point (s) | Gel strength (Pa) |
|---|---|---|
| HA—CDH/HA—NB (2% wt) | 20 | 1250 |
| HA—CDH/Chitosan-NB (2% wt) | 25 | 1506 |
| HA—CDH/Copolymer-NB (5% wt) | 23 | 5030 |
| PEG—ONH$_2$/HA—NB (5% wt) | 28 | 3509 |
| PEG—ONH$_2$/Chitosan-NB (5% wt) | 30 | 4020 |
| PEG—ONH$_2$/Copolymer-NB(10% wt) | 30 | 10065 |
| Gelatin/HA—NB (5% wt) | 28 | 3080 |
| Gelatin/Chitosan-NB (5% wt) | 32 | 4027 |
| Gelatin/Copolymer-NB (5% wt) | 26 | 5490 |

Exemplary Embodiment 13: The Relation Between the Swelling Ratio and the Polymer Concentration of the Hydrogel Prepared by the Non-Free Radical Photocrosslinking Gelation The hydrogels composed of HA-NB (Exemplary Embodiment 1) and HA-CDH (Exemplary Embodiment 2) with polymer concentration of 1% and 2% were exploited to

TABLE 1

| | content B | | | | | | |
|---|---|---|---|---|---|---|---|
| A | HA-CDH | HA-ODH | HA-ADH | PEG-4ONH$_2$ | Dextran-ONH$_2$ | Glycol-Chitosan | Gelatin |
| HA-NB | 0.5-3 wt % | 0.5-3 wt % | 0.5-3 wt % | 1-6 wt % | 0.5-3 wt % | 0.5-3 wt % | 0.5-5 wt % |
| Dextran-NB | 0.5-3 wt % | 0.5-3 wt % | 0.5-3 wt % | 1-6 wt % | 0.5-3 wt % | 0.5-3 wt % | 0.5-5 wt % |
| Chitosan-NB | 0.5-3 wt % | 0.5-3 wt % | 0.5-3 wt % | 1-6 wt % | 0.5-3 wt % | 0.5-3 wt % | 0.5-5 wt % |
| PEG-4NB | 1-6 wt % | 1-6 wt % | 1-6 wt % | 2-30 wt % | 1-6 wt % | 1-6 wt % | 1-10 wt % |
| Copolymer-NB | 1-6 wt % | 1-6 wt % | 1-6 wt % | 2-30 wt % | 1-6 wt % | 1-6 wt % | 1-10 wt % |

Figure 3:
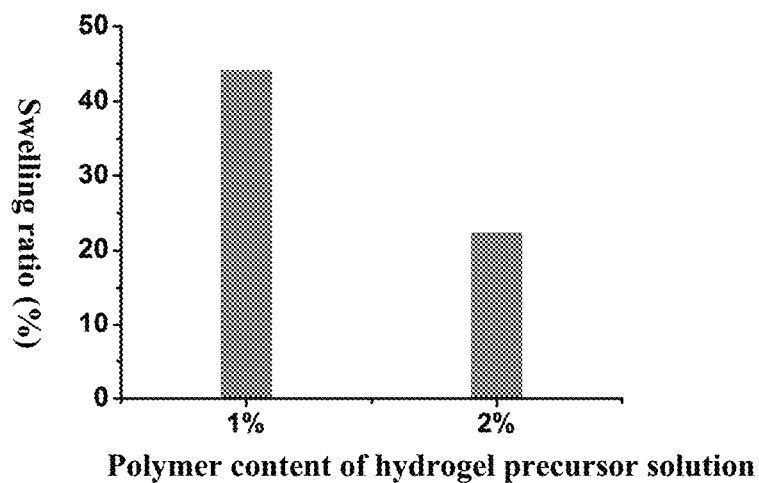
FIG. 3 shows the relationship between the swelling ratio and the polymer content of hydrogel precursor solution (HA-NB+HA-CDH).

The hydrogels with different chemical compositions can be obtained by irradiating the precursor solutions at 365 nm (10 mW cm$^{-2}$) for 30 s-2 min. The hydrogel with different polymer component will exhibit different biological effects. Therefore, polymer components of the non-free radical photo-crosslinking hydrogel can be optimized according to the predesigned intention.

investigate the relation between hydrogel swelling ration and polymer concentration. The swelling ratio of the hydrogels was tested after fully swelling in water for about 24 h. FIG. 3 showed that the hydrogels with lower polymer concentration exhibited higher swelling ratio. On the contrary, hydrogels with higher polymer concentration exhibited lower swelling ratio. It is mainly because that the precursor solution with higher polymer concentration forms a hydrogel with higher crosslinking density, thus resulting in the decrease of its water absorbing capacity.

$$\text{Swelling ratio (\%)} = (W_{Swelling} - W_{Dry})/W_{Dry} \times 100\%$$

In this experiment, the mass of the samples reached equilibrium state after 24 hours immersing in the medium. $W_{Swelling}$ is the gel weight after immersing in the medium for 24 h; $W_{Dry}$ is the gel weight after freeze-drying.

Figure 4:
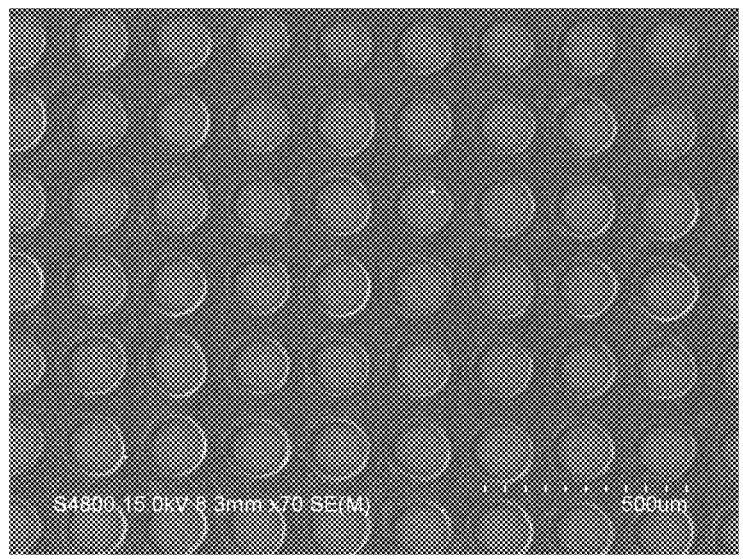
FIG. 4 shows the scanning electron microscope image of the patterned hydrogel (10% wt, copolymer-NB+PEG-4ONH$_2$) obtained from the non-free radical photo-crosslinking methods.

Exemplary Embodiment 14: The Non-Free Radical Photo-Crosslinking Gelation for Hydrogel Pattern Copolymer-NB (Exemplary Embodiment 5) and PEG-ONH$_2$ (Exemplary Embodiment 7) with equal mass were dissolved in distilled water to obtain the hydrogel precursor solution with polymer concentration of 10 wt %. The solution was then tiled onto a glass slide that was pretreated with piranha solution. After that, a chromeplate photomask was placed over the solution in glass slide and the distance between the mask and the glass slide was fixed at about 2 mm. After irradiating with 365 nm 365 nm light (10 mW cm$^{-2}$) for about 30 s-1 min and rinsing with secondary water slowly, the samples was observed by scanning electron microscopy (FIG. 4). The clear pattern in FIG. 4 demonstrates that the non-free radical photocrosslinking gelation has excellent spatiotemporal controllability.

Figure 5:
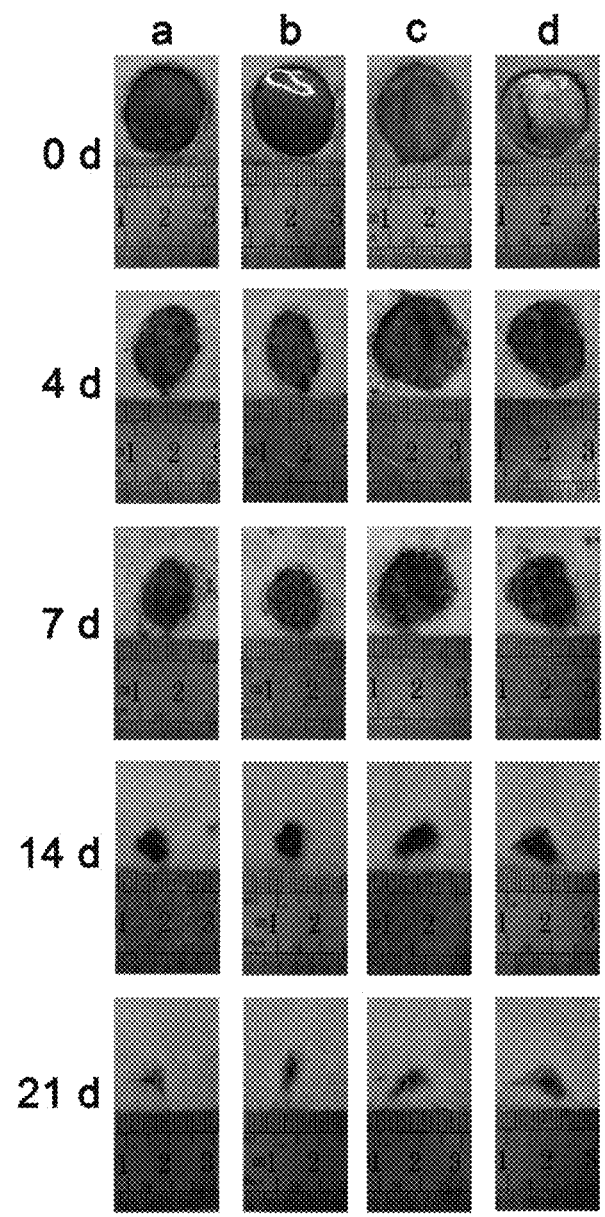
FIG. 5 shows the final healing results of the wounds treated with the non-free radical photo-crosslinking hydrogel on rat skin.

Exemplary Embodiment 15: The Non-Free Radical Photocrosslinking Gelation for the Repair of Skin Wound in SD Rats 4 complete skin defects with 1.8 cm diameter were made on the back of each rats. In order to ensure the faithfulness of the results, four materials (non-free radical photo-crosslinking hydrogels composed of 1% wt (a) or 2% (b) wt HA-NB and HA-CDH hydrogel; (c) commercialized 3M artificial skin; (d) no material treating) were respectively added to cover the four defects in one rat. The healing results of the defects were evaluated by microscopic observation and histological analysis. As shown in FIG. 5, the healing results of the defects treated by the non-free radical photo-crosslinking hydrogels (a, b) were much better than that of 3M artificial skin treated defects and sham control defect, suggesting the promotion effect of the non-free radical photo-crosslinking materials on wound repair. Furthermore, histological analysis results indicated that there was no obvious inflammation cells, demonstrating the biocompatibility of the hydrogel.

Figure 6:
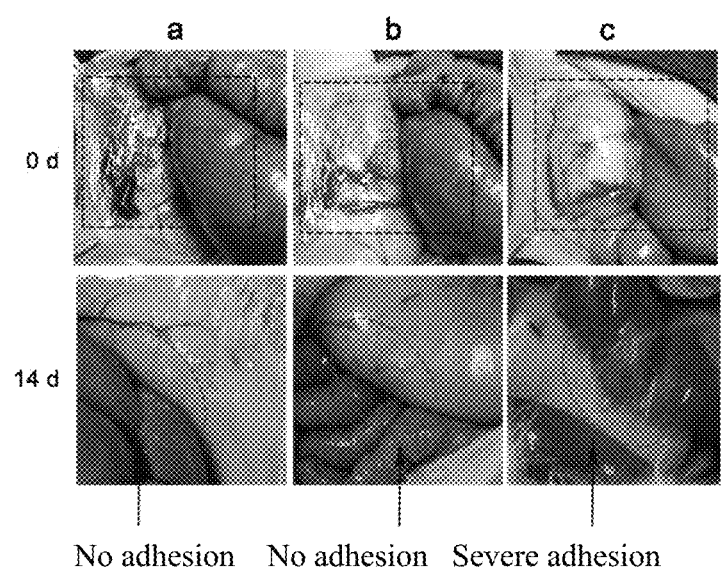
FIG. 6 shows the anti-adhesion effect of the non-free radical photo-crosslinking hydrogel on the rabbit abdominal defect model.

Exemplary Embodiment 16: The Non-Free Radical Photocrosslinking Gelation for Postsurgical Anti-Adhesion Defects were made in the abdominal wall and cecum of the New Zealand rabbits (n=30). Then they were averagely and randomly divided into three groups based on the treatment of the defects: a. in situ formed HA-NB and HA-CDH hydrogel (2% wt); b. clinical used anti-adhesion film group; c. rising with saline. 14 days after surgery, all the rabbits were sacrificed by venous air embolism and the abdominal tissue adhesion result of each rabbit was evaluated. As shown in FIG. 6, serious tissue adhesion was observed in the rabbits from the sham control group (c). While, nine out of ten rabbits in the experiment group (a) developed no tissue adhesion at all and very slight adhesion was observed in the other rabbit of this group. In addition, no inflammation cells were observed in the histological staining image of the experiment group. These results demonstrate that hydrogel formed by the non-free radical photo-crosslinking method exhibits excellent biocompatibility and anti-adhesion ability.

Exemplary Embodiment 17: Non-Free Radical Photo-Crosslinking Gelation for Cell, Protein and Drug Delivery Due to the unique properties of the non-free radical photocrosslinking gelation, it can achieve the in situ encapsulation of cell, protein and drug in hydrogel. Thus, the hydrogels prepared by this methods can be used as cell biology platform to mimic the natural extracellular matrix to manipulate cell fates by controlling the gel strength such as the differentiation of stem cells; it can also be used as in vivo controlled delivery systems for proteins and drugs. Next, we will introduce the application of the hydrogel prepared by the non-free radical photo-crosslinking gelation as a 3D scaffold material for mimicking the natural ECM. Equal weight of HA-NB and glycol chitosan was dissolved in α-MEM to prepare the hydrogel precursor solution. Mesenchymal stem cells were digested from plates by trypsin and centrifuged, and then added to the hydrogel precursor solution to get uniform cell suspension with a density 4×10$^6$ cells/mL. After that, 25 μL above cell suspension was added into a 24-well plate and the suspension was further irradiated by 365-nm light of different time to form cell-encapsulated hydrogel with various gel strength. Next, the culture medium, antibiotics and culture was added to each well and the cells were cultured under the condition of 37° C., 5% CO$_2$. Finally, the impacts of hydrogel strength on the biochemical properties of MSCs was evaluated according to the reported methods in the following reference: C. Yang, M. W. Tibbitt, L. Basta, K. S. Anseth, *Nat. Mater.* 2014, 13, 645-652; O. Jeon, D. S. Alt, S. W. Linderman, E. Alsberg, *Adv. Mater.* 2013, 25, 6366-6372.

Exemplary Embodiment 18: Application of the Non-Free Radical Photo-Crosslinking for the Moisturizing, Whitening and Anti-Wrinkle of Skin Hyaluronic acid can make skin soft and smooth, increasing the elasticity and preventing the aging of skin largely exists in skin. Gelatin is the degradation product of collagen and has been widely used in cosmetology. Considering the easy operation and in situ controllability of the non-free radical photo-crosslinking gelation method, it can be used to prepare hydrogel mask containing hyaluronic acid and gelatin. For example, HA-NB (Exemplary Embodiment 11) can be used in combination with gelatin to produce hydrogel mask under light irradiation. This hydrogel mask can be formed directly on a face under light irradiation, adapting to profile of the face. Furthermore, essence factors can also be added into the HA-NB/gelatin hydrogel mask during its photo gelation process. Consequently, this hydrogel mask can perfectly attach the skin to preserve moisture, while the essence encapsulated in hydrogel mask can also be released to achieve better cosmetic effect.

The invention claimed is:

1. A preparation method of hydrogel by non-free radical photo-crosslinking reaction, comprising:
    obtaining solution A by dissolving component A in biocompatible medium, and obtaining solution B by dissolving component B that is a polymer derivative containing hydrazide, hydroxylamine or primary amine in biocompatible medium;

obtaining a precursor solution of hydrogel by mixing solution A and solution B homogeneously;

crosslinking the precursor solution to form a hydrogel under light irradiation via reacting aldehyde groups generated from o-nitrobenzyl of the component A after photo-activation with hydrazine, hydroxylamine, or primary amine groups of the component B, the reaction between the aldehyde groups and the hydrozin, hydroxylamine, or primary amine groups forming hydrazone, oxime and schiff base, respectively, wherein the component A is a derivative of a polymer modified with o-nitrobenzyl phototrigger as shown in structural formula I:

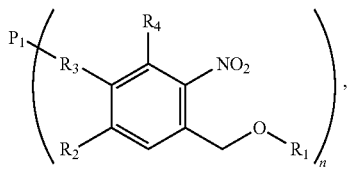

where $R_1$ is —H, ester bond selected from —CO(CH$_2$)$_x$CH$_3$, —CO(CH$_2$CH$_2$O)$_x$CH$_3$, —CO(CH$_2$)$_x$(CH$_2$CH$_2$O)$_y$CH$_3$, ether bond selected from —(CH$_2$)$_x$CH$_3$, —(CH$_2$CH$_2$O)$_x$CH$_3$, —(CH$_2$)$_x$(CH$_2$CH$_2$O)$_y$CH$_3$,

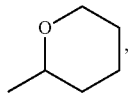

carbonic ester bond selected from —COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$, or carbamate bond selected from —CONH(CH$_2$)$_x$CH$_3$, —CONH(CH$_2$CH$_2$O)$_x$CH$_3$, —CONH(CH$_2$)$_x$(CH$_2$CH$_2$O)$_y$CH$_3$, where the x and y≥0 and are integer;

$R_2$ is —H or substituent group selected from —O(CH$_2$)$_x$CH$_3$, —O(CH$_2$CH$_2$O)$_x$CH$_3$, —O(CH$_2$)$_x$(CH$_2$CH$_2$O)$_y$CH$_3$, where the x and y≥0 and are integer;

$R_3$ is selected from amino linkage bond —O(CH$_2$)$_x$CONH(CH$_2$)$_y$NH—, halogenated linkage bond —O(CH$_2$)$_x$— and carboxyl linkage bond —O(CH$_2$)$_x$CO—, wherein the ether bond end of $R_3$ being connected with the benzene ring of the structural formula I and the other end of $R_3$ being connected with $P_1$, x and y≥1 and being integer;

$R_4$ is —H or —CONH(CH$_2$)$_x$CH$_3$, where the x≥0 and being integer;

$P_1$ is hydrophilic or water-soluble natural polysaccharide, protein or polypeptide, or hydrophilic or water-soluble synthetic polymer, wherein the component B is a polymer derivative containing hydrazide, hydroxylamine, or primary amine, as shown in structural formula IIA, IIB, IIC, respectively:

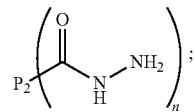

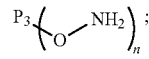

wherein n≥2, $P_2$, $P_3$, $P_4$ each independently are hydrophilic or water-soluble natural polysaccharide, protein, polypeptide, or hydrophilic or water-soluble synthetic polymer.

2. The preparation method of claim 1, wherein the natural polysaccharide is selected from hyaluronic acid, alginate, heparin, dextran, carboxymethyl cellulose, glycol chitosan, propylene glycol chitosan, chitosan lactate, carboxymethyl chitosan, chitosan quaternary ammonium salt, and a modified derivative or degradation product thereof;

the protein or polypeptide is selected from all kinds of hydrophilic or water-soluble plant or animal protein, collagen, serum protein, gelatin, and a modified derivative or degradation peptide thereof, the hydrophilic or water-soluble synthetic polymer is selected from two or multi-arms polyethylene glycol, polyethyleneimine, dendrimer, synthetic peptide, polylysine, (methyl) acrylate or (methyl) acrylamide polymer, and a modified derivative thereof.

3. The preparation method of claim 1, wherein the biocompatible medium is at least one medium selected from the group consisting of distilled water, saline, buffer, and cell culture medium solution.

4. The preparation method of claim 1, wherein, in the precursor solution of hydrogel, a molar ratio of the o-nitrobenzyl group to the hydrazine or hydroxylamine or primary amine group is from 1:0.02 to 1:50, preferably from 1:0.1 to 1:10; a total concentration of polymer is from 0.1 wt % to 60 wt %, preferably from 1 wt % to 10 wt %.

5. The preparation method of claim 1, wherein the illumination wavelength of the light source is 250 nm to 500 nm, preferably 300 nm to 400 nm, more preferably 365 nm.

6. A non-free radical photo-crosslinking hydrogel prepared according to the preparation method of claim 1.

7. A kit for preparing hydrogel through non-free radical photo-crosslinking using the method of claim 1, comprising:

component A that is a derivative of a polymer modified with o-nitrobenzyl phototrigger shown as formula I;

component B that is a polymer derivative containing hydrazide, hydroxylamine or primary amine as shown as formula IIA, IIB, or IIC; and instructions about the preparation and application of hydrogel.

8. The kit of claim 7, wherein the kit further includes a biocompatible medium including buffer and cell culture medium.

9. The kit of claim 7, wherein the instructions further include description of applications of hydrogel in tissue repair, beauty therapy, and cells, proteins or drugs carriers.

* * * * *